(12) United States Patent
Quesada et al.

(10) Patent No.: US 7,940,105 B2
(45) Date of Patent: May 10, 2011

(54) HIGH-RESOLUTION PARAMETRIC SIGNAL RESTORATION

(75) Inventors: Valentin T. Quesada, Miami Lakes, FL (US); Bruce M. Weber, Cooper City, FL (US)

(73) Assignee: Beckman Coulter, Inc., Brea, CA (US)

( * ) Notice: Subject to any disclaimer, the term of this patent is extended or adjusted under 35 U.S.C. 154(b) by 26 days.

(21) Appl. No.: 12/189,028

(22) Filed: Aug. 8, 2008

(65) Prior Publication Data

US 2010/0033231 A1 Feb. 11, 2010

(51) Int. Cl.
*H03L 5/00* (2006.01)
(52) U.S. Cl. ............................................. 327/307; 330/9
(58) Field of Classification Search .................. 327/307; 330/9
See application file for complete search history.

(56) References Cited

U.S. PATENT DOCUMENTS

| | | | |
|---|---|---|---|
| 3,525,948 A * | 8/1970 | Halverson et al. | ............... 330/51 |
| 3,733,547 A | 5/1973 | Coulter et al. | |
| 3,987,242 A | 10/1976 | Gold | |
| 4,007,376 A | 2/1977 | Zimmerman | |
| 4,010,366 A | 3/1977 | Neukermans | |
| 4,024,398 A | 5/1977 | Hatch | |
| 4,053,767 A | 10/1977 | Kampfer | |
| 4,055,762 A | 10/1977 | Durkin | |
| 4,065,790 A | 12/1977 | Siegel | |
| 4,093,876 A | 6/1978 | Henein et al. | |
| 4,110,604 A | 8/1978 | Haynes et al. | |
| 4,125,812 A | 11/1978 | Polonio | |
| 4,165,484 A | 8/1979 | Haynes | |
| 4,182,314 A | 1/1980 | Boughton | |
| 4,198,703 A | 4/1980 | Huisveld, Jr. et al. | |
| 4,227,405 A | 10/1980 | West | |
| 4,240,029 A | 12/1980 | Haynes | |
| 4,293,815 A | 10/1981 | West et al. | |
| 4,317,137 A | 2/1982 | Tompkins | |
| 4,373,140 A | 2/1983 | Chin | |
| 4,375,615 A | 3/1983 | Haynes | |
| 4,375,645 A | 3/1983 | Funatsu | |
| 4,378,571 A | 3/1983 | Handy | |
| 4,415,266 A | 11/1983 | Matthews et al. | |
| 4,429,997 A | 2/1984 | Matthews | |

(Continued)

FOREIGN PATENT DOCUMENTS

WO WO 2005/091893 A2 10/2005

OTHER PUBLICATIONS

Jung, W., "IC Op-Amp Handbook—Second Edition," Howard W. Sams & Co., Inc.; 1981, pp. 203-204.

(Continued)

*Primary Examiner* — Kenneth B. Wells
(74) *Attorney, Agent, or Firm* — Sterne, Kessler, Goldstein & Fox, P.L.L.C.

(57) ABSTRACT

Provided are high-resolution parametric signal restoration systems, and applications thereof. Such systems include a multi-output module and a parametric compensator. The multi-output module provides a reference gain output signal and one or more higher gain output signals based on a single input signal. The parametric compensator independently responds to functional parameters of the one or more higher gain output signals to provide a compensation error signal. The single input signal is modified based on the compensation error signal.

18 Claims, 13 Drawing Sheets

U.S. PATENT DOCUMENTS

| | | |
|---|---|---|
| 4,481,466 A | 11/1984 | Roos et al. |
| 4,481,535 A | 11/1984 | Hodd et al. |
| 4,549,214 A | 10/1985 | Hinn |
| 4,654,712 A | 3/1987 | Gershfeld |
| 4,680,633 A | 7/1987 | Gerdes et al. |
| 4,727,256 A | 2/1988 | Kumazawa |
| 5,055,675 A | 10/1991 | Bridges |
| 5,125,737 A | 6/1992 | Rodriguez et al. |
| 5,268,575 A | 12/1993 | Tajima |
| 5,309,357 A | 5/1994 | Stark et al. |
| 5,418,608 A | 5/1995 | Caimi et al. |
| 5,546,048 A | 8/1996 | Sano et al. |
| 5,610,967 A | 3/1997 | Moorman et al. |
| 5,616,501 A | 4/1997 | Rodriguez et al. |
| 5,631,165 A | 5/1997 | Chupp et al. |
| 5,644,612 A | 7/1997 | Moorman et al. |
| 5,651,047 A | 7/1997 | Moorman et al. |
| 5,656,499 A | 8/1997 | Chupp et al. |
| 5,729,584 A | 3/1998 | Moorman et al. |
| 5,751,785 A | 5/1998 | Moorman et al. |
| 5,805,281 A | 9/1998 | Knowlton et al. |
| 5,812,419 A | 9/1998 | Chupp et al. |
| 5,835,561 A | 11/1998 | Moorman et al. |
| 5,859,893 A | 1/1999 | Moorman et al. |
| 5,891,734 A | 4/1999 | Gill et al. |
| 5,939,326 A | 8/1999 | Chupp et al. |
| 6,091,025 A | 7/2000 | Cotter et al. |
| 6,173,036 B1 | 1/2001 | Hossain et al. |
| 6,204,668 B1 | 3/2001 | Sequeira et al. |
| 6,239,379 B1 | 5/2001 | Cotter et al. |
| 6,241,920 B1 | 6/2001 | Cotter et al. |
| 6,363,111 B1 * | 3/2002 | Hee et al. ............ 375/224 |
| 6,438,193 B1 | 8/2002 | Ko et al. |
| 6,528,814 B1 | 3/2003 | Frank et al. |
| 6,635,892 B2 | 10/2003 | Kelly, Jr. et al. |
| 6,649,914 B1 | 11/2003 | Moorman et al. |
| 6,684,030 B1 | 1/2004 | Taylor et al. |
| 6,714,878 B2 * | 3/2004 | Vyers ............ 702/45 |
| 6,781,134 B1 | 8/2004 | Murray et al. |
| 6,822,506 B2 | 11/2004 | Binkley |
| 6,879,300 B2 * | 4/2005 | Rochelle et al. ............ 343/867 |
| 6,977,502 B1 * | 12/2005 | Hertz ............ 324/318 |
| 7,117,186 B2 * | 10/2006 | Koza et al. ............ 706/13 |
| 7,142,167 B2 | 11/2006 | Rochelle et al. |

OTHER PUBLICATIONS

"The Handbook of Linear IC Applications," Burr-Brown Corporation; 1987, pp. 180-181.

"Wide-Bandwidth, DC Restoration Circuit," Texas Instruments; 2004, pp. 1-30.

Bevensee et al., "An Amplifier-Shaper-Discriminator with Baseline Restoration for the ATLAS Transition Radiation Tracker," IEEE Transactions on Nuclear Science, vol. 43 No. 3, Jun. 1996, pp. 1725-1731.

Geromino, et al., "A CMOS Baseline Holder (BLH) for Readout ASICs," IEEE Transactions on Nuclear Science, vol. 47 No. 3, Jun. 2000, pp. 818-822.

Fairstein, E., "Gated Baseline Restorer with Adjustable Asymmetry," IEEE Transactions on Nuclear Science, vol. NS-22, Feb. 1975, pp. 463-466.

Morgado et al., "A Pulse Processing Station," IEEE, 1997, pp. 490-493.

Pullia, A., "The "switch off" baseline restorer for the 120 channel silicon detector system for EXAFS at NSLS," Nuclear Instruments and Methods in Physics Research A 370, 1996, pp. 490-498.

Wood, J., "Fundamental Flow Cytometer Properties Governing Sensitivity and Resolution," Cytometry, vol. 33, 1998, pp. 260-266.

Beckman Coulter, CoulterCounter.com, "*Multisizer*$_{TM}$*3 Coulter Counter* ", 7 pages, printed from http://www.beckmancoulter.com/coultercounter/product_multisizer3.jsp, printed on Feb. 2, 2009.

* cited by examiner

HIGH-RESOLUTION PARAMETRIC SIGNAL RESTORATION

BACKGROUND OF THE INVENTION

1. Field of the Invention

The present invention is generally directed to the field of particle analyzers, such as flow cytometers and hematology instruments. More particularly, it is directed to processing signals from particle analyzers.

2. Background Art

Instruments are often used to detect or measure physical events and to convert the detected physical events into electronic signals. For example, a flow cytometer is an instrument used to characterize particles. In flow cytometry, the particles are made to flow in a controlled environment and are (principally) illuminated by a laser. When a detectable physical event occurs, the flow cytometer converts that physical event into an electronic signal.

The detectable physical events are often represented as time-varying pulses that appear above DC offsets and noise. The DC component of these electronic signals is often unwanted. Removal of the DC component of these electronic signals should be performed without compromising the fidelity of the time-varying component of the electronic signals.

AC coupling circuits are special circuits that remove the DC component from time-varying signals. These coupling circuits can be very simple (such as a single capacitor) or very complex. The complexity of such circuits is typically a function of the performance requirements of the measurement system. These requirements become more demanding when the input signal is a pulse rather than a repetitive signal such as a sine wave.

Existing measurement systems in flow cytometers and hematology instruments are equipped with complex restoration circuitry that restores a signal baseline. The signal baseline is a reference point; signals above the baseline are positive and signals below the baseline are negative. The restored signal is then measured by an acquisition system. In flow cytometry the results of the acquired measurement may be displayed on a log-histogram plot, which displays particle counts versus signal intensity.

Existing restoration circuitry may use a rectification technique or a noise-centering technique. A rectification technique places the system noise in the active polarity region of the reference baseline. With a noise-centering technique only half of the noise population is above the signal baseline. The other half is "buried" since the acquisition system cannot convert negative values. Existing restoration circuits typically have a single amplitude output. A problem with this type of existing restoration circuit, however, is that it may not provide the requisite dynamic range and fidelity for use in certain types of flow cytometry and hematology instruments.

Given the foregoing, what is needed are high-resolution parametric signal restorers, and applications thereof. Such high-resolution parametric signal restorers should advantageously increase the uni-polar dynamic range of input signals, while suppressing the opposite polarity signals.

BRIEF SUMMARY OF THE INVENTION

The present invention provides high-resolution parametric signal restorers, and applications thereof. Such high-resolution parametric signal restorers derive a low-gain output signal and one or more high-gain output signals from an input signal. Such high-resolution parametric signal restorers may be used, for example, in cytometry and/or hematology instruments.

Embodiments of the present invention provide systems and methods for processing electronic signals. Such systems include a multi-output module and a parametric compensator. The multi-output module provides a reference gain output signal and one or more higher gain output signals based on an input signal. In embodiments, the parametric compensator independently responds to functional parameters of the one or more higher gain output signals to provide a compensation error signal. The input signal is modified based on the compensation error signal.

Another embodiment of the present invention provides a series embodiment of a high-resolution signal restoration system for processing signals from a measurement instrument. This embodiment includes a first combining module, a first amplifier, a second amplifier, and a feedback. The first combining module combines an input signal and a compensation error signal to provide a combined signal. The first amplifier has a first gain to provide a first amplified signal based on the combined signal. The second amplifier has a second gain that is different from the first gain to provide a second amplified signal based on the combined signal. The feedback generates the compensation error signal based on the second amplified signal.

In one embodiment, the feedback includes a first direct current (DC) restoration module and a second DC restoration module. The first DC restoration module has a first time constant and may be configured to reduce a DC component of the second amplified signal to provide a first processed signal. The second DC restoration module has a second time constant that is different from the first time constant and may be configured to reduce the DC component of the second amplified signal to provide a second processed signal. The feedback output module provides a compensation error signal. The compensation error signal may comprise either the first processed signal or a combination of the first and second processed signals.

A further embodiment of the present invention provides a shunt embodiment of a high-resolution signal restoration system for processing signals from a measurement instrument. This embodiment includes an AC coupling, a first amplifier, a second amplifier, a pulse undershoot module, a feedback, and a summation module. The first amplifier has a first gain to provide a first amplified signal based on an input signal received via the AC coupling. The second amplifier has a second gain that is different from the first gain to provide a second amplified signal based on the input signal received via the AC coupling. The pulse undershoot module is coupled to the AC coupling to reduce pulse undershoot recovery time after the AC coupling. The feedback generates a compensation error signal based on the second amplified signal. The summation module adds the compensation error signal to the input signal received by the first and second amplifiers.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIG. 1 illustrates an example system for analyzing particles.

Figure 8:
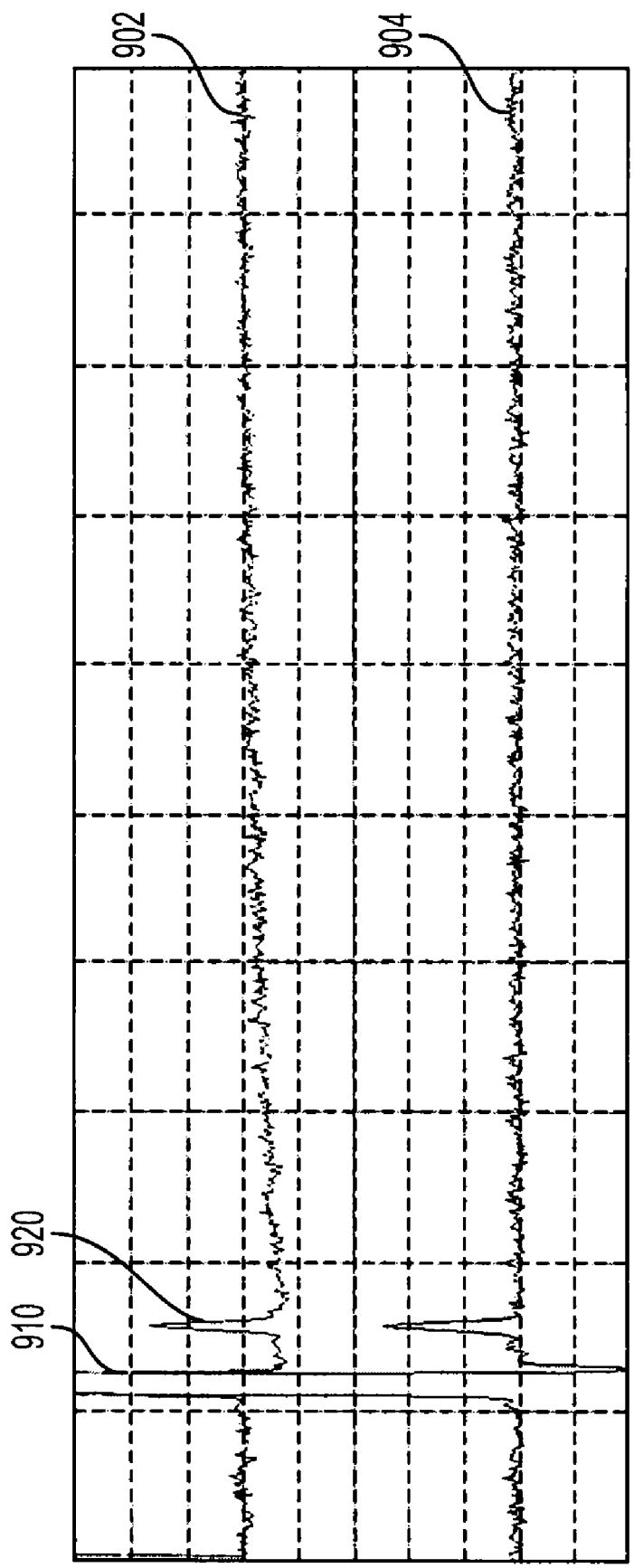

FIG. 8 graphically illustrates the operation of a pulse undershoot recovery module in accordance with an embodiment of the present invention.

Figure 6:
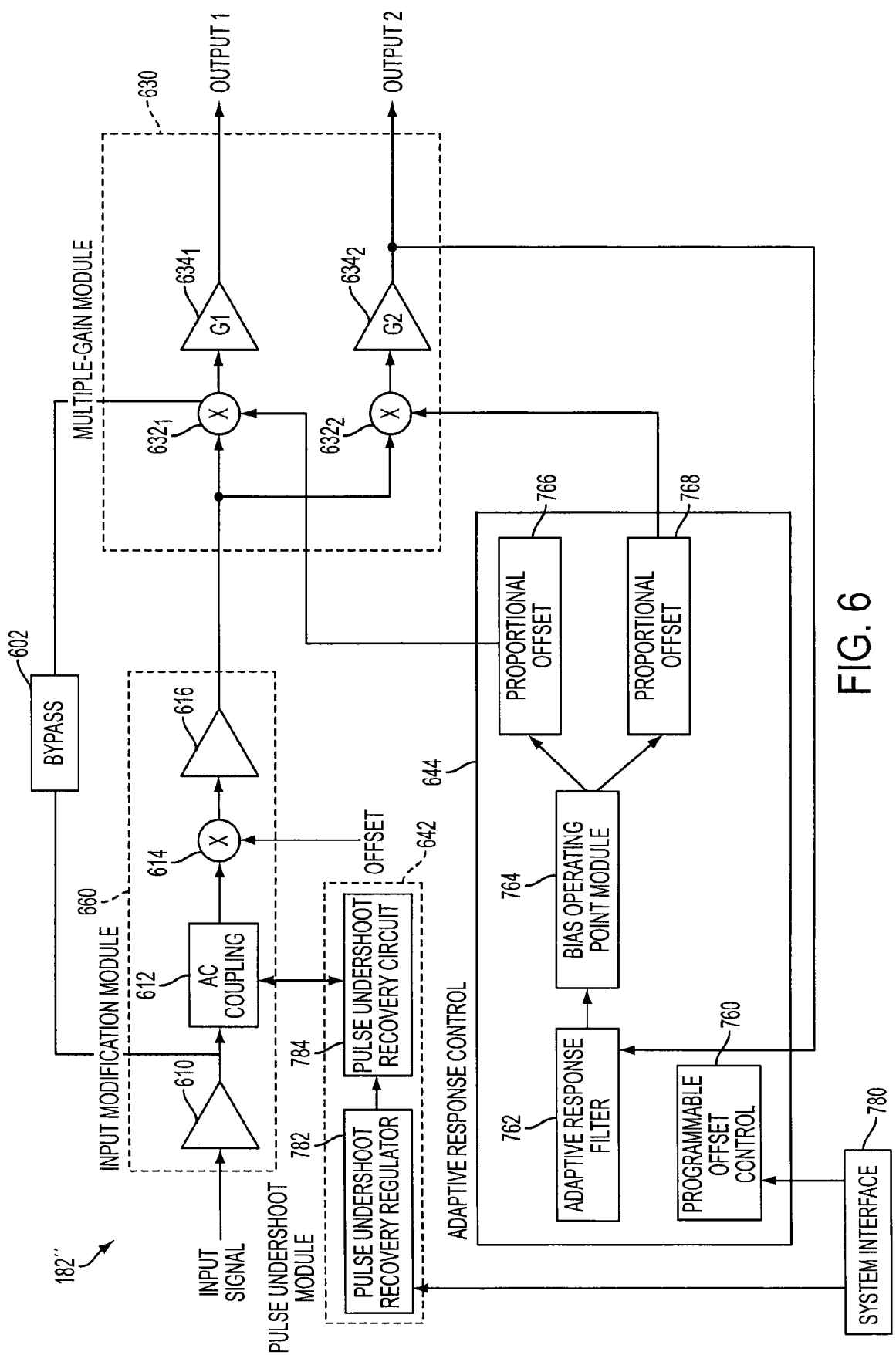
FIG. 6 illustrates a more detailed example of the high-resolution parametric signal restorer of FIG. 5.
Figure 9A:
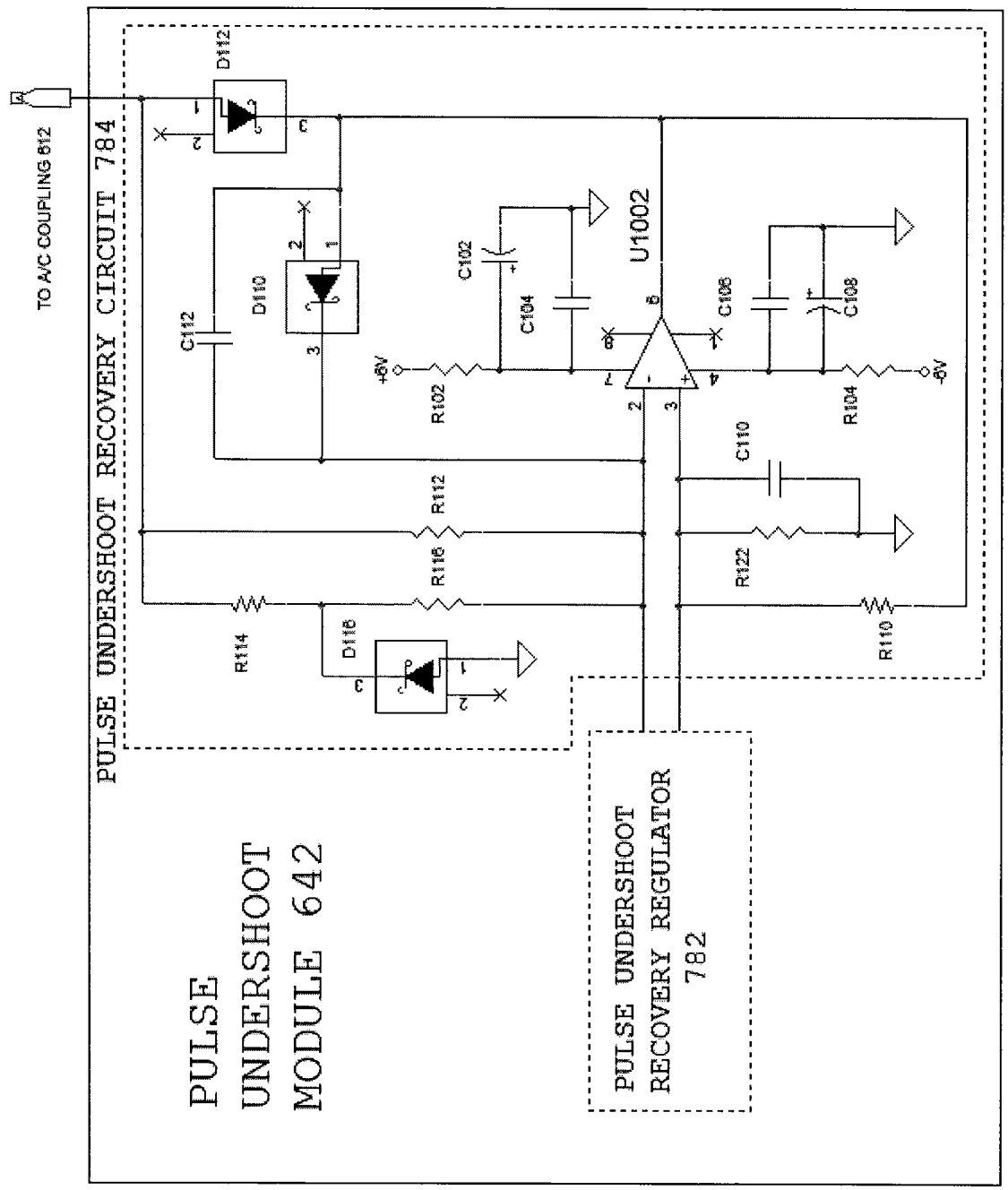
Figure 9B:
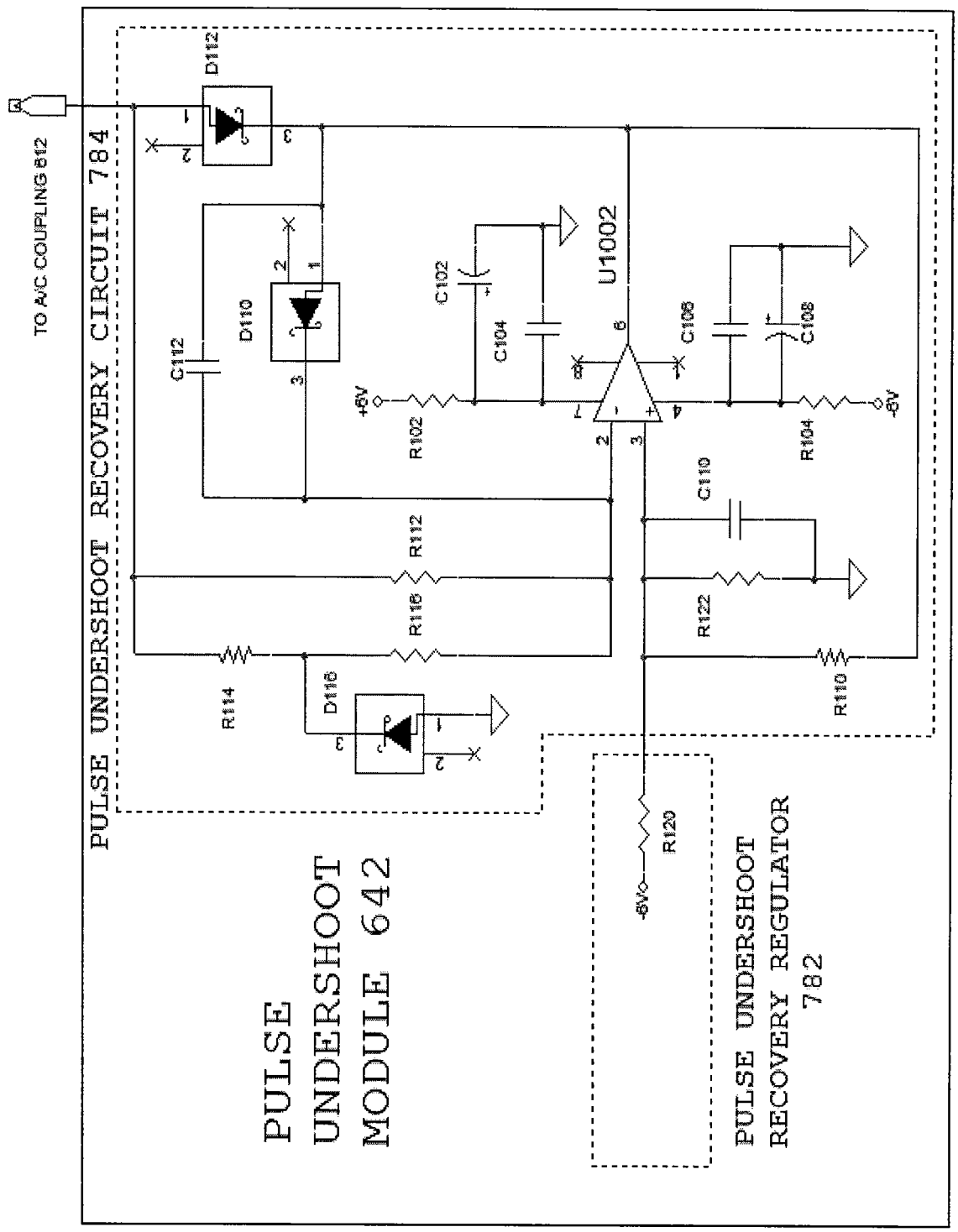
Figure 9C:
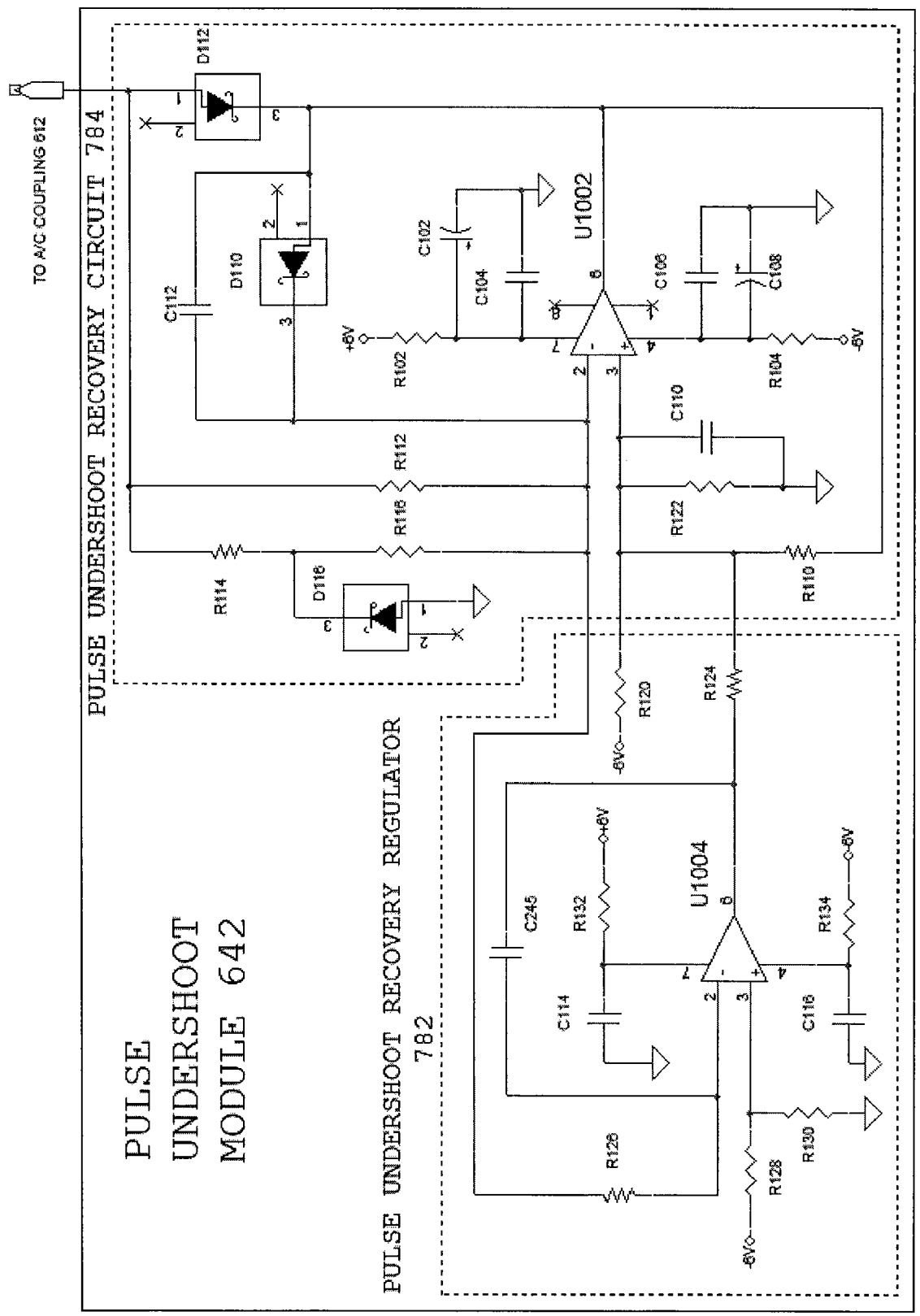

FIGS. 9A, 9B, and 9C illustrate embodiments of the pulse undershoot module depicted in the high-resolution parametric signal restorer of FIG. 6.

Figure 10:
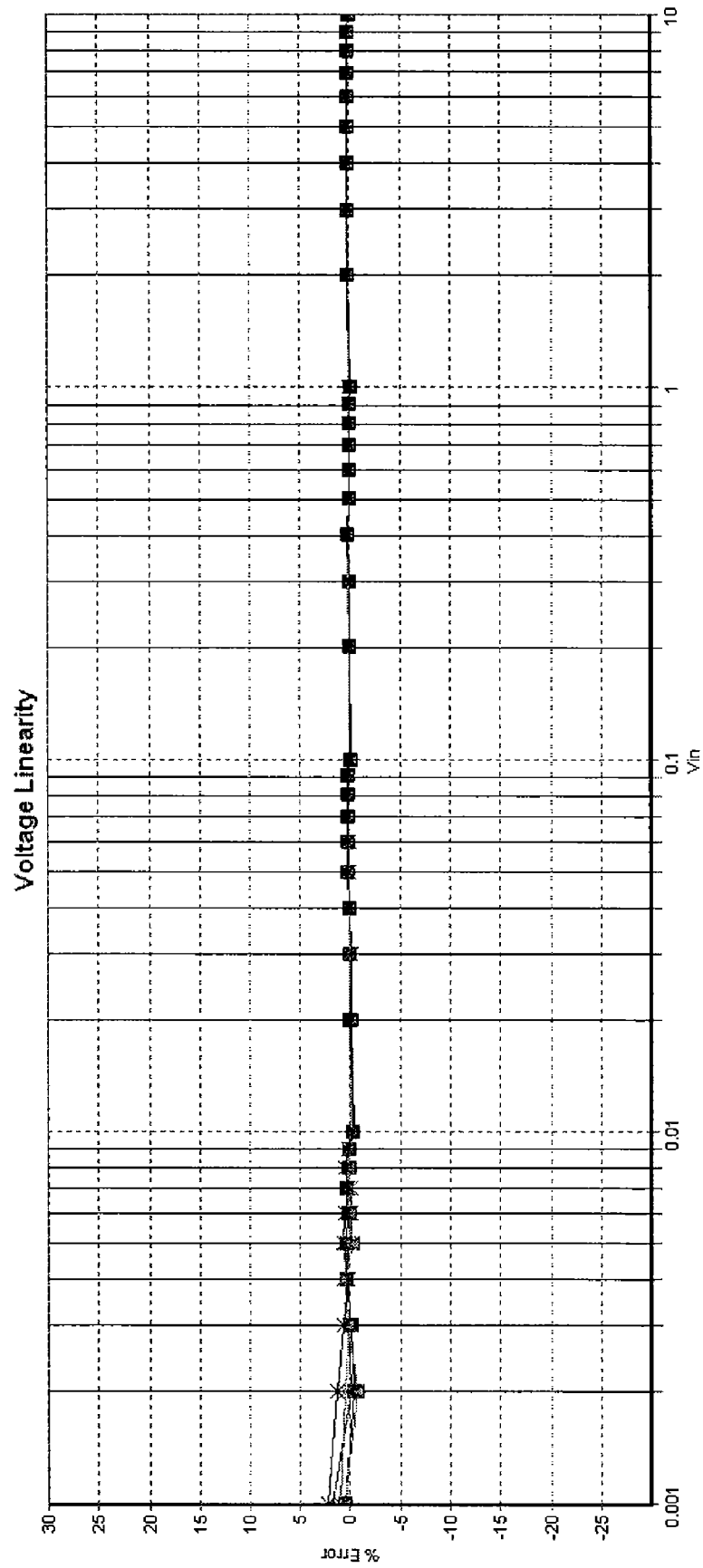

FIG. 10 depicts a graph illustrating example signal linearity measurements.

FIGS. 11A, 11B, 11C, and 11D illustrate how an adaptive response filter and bias operating point module function to reduce an average noise level with respect to a capture window.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

The present invention provides high-resolution parametric signal restorers, and applications thereof. In the detailed description that follows, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

A high-resolution parametric signal restorer in accordance with an embodiment of the present invention processes signals from sensors which convert physical events to electronic signals. Due to the configuration of the sensors, the electronic signals typically include an AC (time-varying) component and a DC (time-invariant) component. The DC component has the net effect of reducing or even eliminating the dynamic range of an acquisition system, making it an unnecessary component of the measured event. The time-varying component of the signal, such as a pulse event, is typically the information of interest. For example, the time-varying component may correspond to the detection of a particle in a flow cytometer or hematology instrument. In addition, the fidelity of processed output signal is an important factor in the accurate measurement of the physical event.

A high-resolution parametric signal restorer in accordance with an embodiment of the present invention is a complete active circuit. The high-resolution parametric signal restorer of this embodiment seeks to provide input signal isolation, maintain input signal fidelity (a short-duration pulse), provide for the dynamic range requirement of an acquisition system, provide multiple linked outputs, and provide a high processing throughput. The high-resolution parametric signal restorer processes substantially Gaussian-shaped pulses, which are typically two microseconds wide at the half-height amplitude and approximately six microseconds wide at the base. The high-resolution parametric signal restorer substantially removes a DC component from sensor signals ranging from micro volts to volts. The high-resolution parametric signal restorer may also cover an operational dynamic range of more than four decades.

In an embodiment, the high-resolution parametric signal restorer provides two or more linked and processed outputs—one output at reference gain and the other(s) at higher gain(s). The reference gain output tracks the higher gain output(s). The high-resolution parametric signal restorer includes a parametric compensator that adjusts performance in the presence of signal content perturbations (such as DC, noise, and signal undershoot). The parametric compensator may include time constants, limiting circuits, error gains, temperature mitigation and other techniques, as described in more detail below.

I. Example Environment

Before describing embodiments of the high-resolution parametric signal restorers in detail, it is helpful to present an example environment in which such high-resolution parametric signal restorers may operate. For illustrative purposes only, and not limitation, a high-resolution parametric signal restorer in accordance with an embodiment of the present invention is described in terms of an example flow cytometry environment. A person skilled in the relevant art(s) will appreciate, however, that high-resolution parametric signal restorers may be implemented in other types of environments and/or systems without deviating from the spirit and scope of the present invention. Such other types of environments and/or systems may include, but are not limited to, hematology instruments, particle detectors, and other types of instruments that convert physical events to electrical signals.

A. Overview

Figure 1:
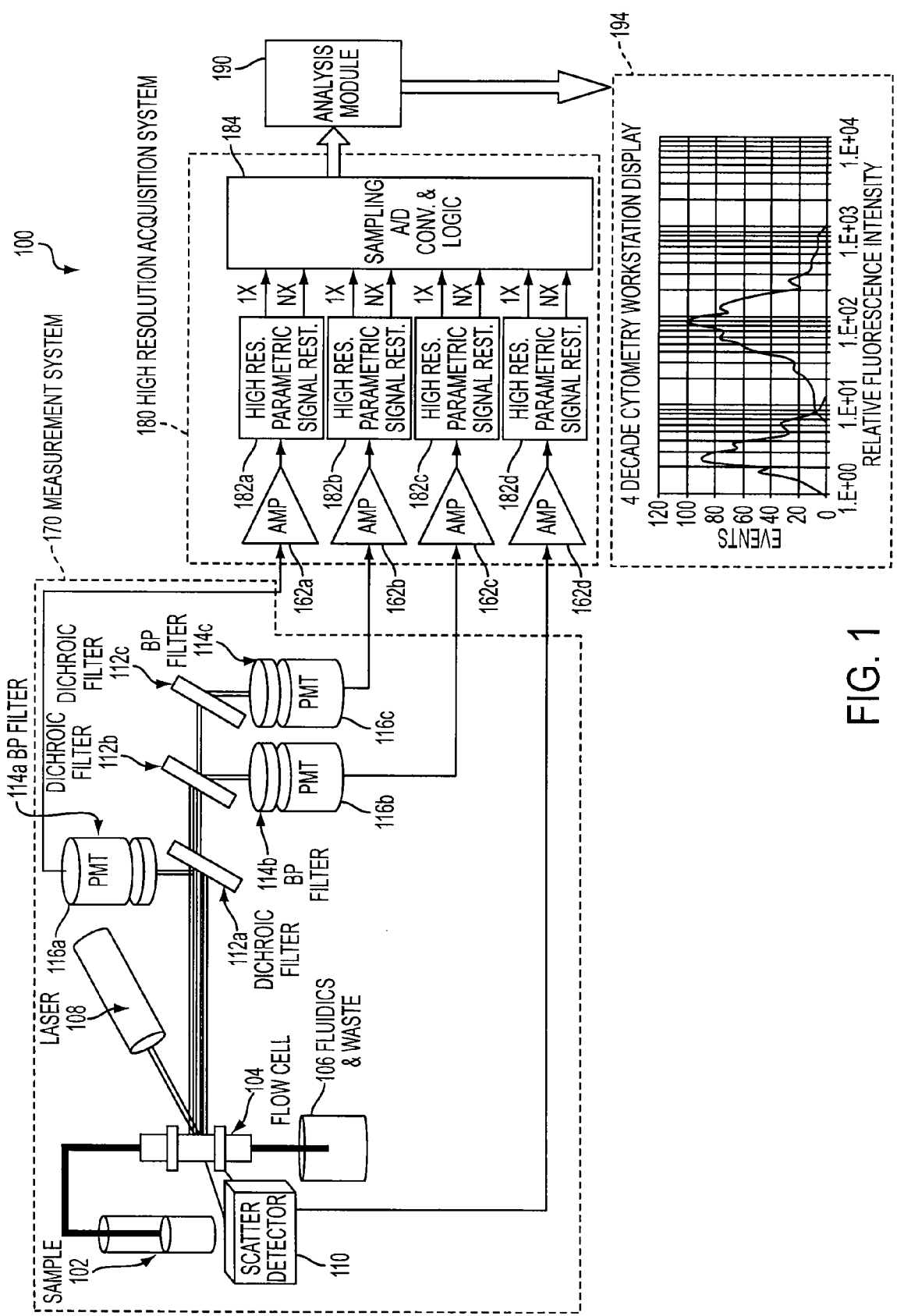

FIG. 1 shows an exemplary system 100 that uses a high-resolution parametric signal restorer in accordance with an embodiment of the present invention. Exemplary system 100 can be used to measure and analyze particle parameters. For example, system 100 may be used in flow cytometry and/or hematology. System 100 includes a measurement system 170, a high-resolution acquisition system 180, and an analysis module 190.

B. Measurement System 170

Measurement system 170 detects physical events and converts the detected physical events into electronic signals. In the embodiment depicted in FIG. 1, measurement system 190 is configured to detect particles suspended in a sample 102. Measurement system 190 may be configured, however, to detect other types of physical events as would be apparent to a person skilled in the relevant art(s). Referring to FIG. 1, measurement system 170 includes a flow cell 104, a laser 108, and photo-multiplier tubes (PMTs) 116a,b,c.

Flow cell 104 receives sample 102. As mentioned above, sample 102 contains particles suspended in a fluid. The particles may comprise, for example, biological cells (such as blood cells), silica particles, clay particles, pellets, latex particles, a combination of any of the foregoing particle types, or any other type of particle capable of being measured by flow cytometry instruments. Sample 102 is aspirated into flow cell 104 and passed into fluidics and waste 106.

Laser 108 illuminates sample 102 as it flows through flow cell 104. Scatter detector 110 detects the laser light that is scatter off sample 102 and converts the scattered laser light into an electrical signal, which is then passed to amplifier 162d of high-resolution acquisition system 180.

It is given that the incident laser light is blocked reaching the PMT 116 by an optical filter (not shown) and that each PMT 116 is allowed to receive a unique range of wavelengths of the fluorescence light emitted by the sample. For example, dichroic filter 112a may be configured to direct a first bandwidth of emitted fluorescence light toward bandpass (BP) filter 114a, which passes the first bandwidth of emitted fluorescence light to PMT 116a. In a similar manner, dichroic filter 112b may be configured to directed a second bandwidth of emitted fluorescence light toward BP filter 114b, which passes the second bandwidth of emitted fluorescence light to PMT 116b; and dichroic filter 112c may be configured to directed a third bandwidth of emitted fluorescence light toward BP filter 114c, which passes the third bandwidth of emitted fluorescence light to PMT 116c. Each PMT 116 is configured to convert the particular bandwidth of emitted fluorescence light it receives into an electrical signal. The electrical signals are then passed to amplifiers 162 of high-resolution acquisition system 180.

It should be noted that the above description relating to measurement system 170 is exemplary, and only for the purposes of illustration. In general, a flow cytometer and/or hematology instrument may use a variety of methods for detecting particles including methods based on the use of fluorescence, light scattering, pyrometry, lasers, and other methods as would be apparent to a person skilled in the relevant art(s). The below-described high-resolution parametric signal restorer, and applications thereof, may be adapted for use in the various types of flow cytometers and hematology instruments.

C. High-Resolution Acquisition System 180

High-resolution acquisition system 180 receives the analog signals from measurement system 170 and converts these analog signals into digital signals. Referring to FIG. 1, high-resolution acquisition system 180 includes amplifiers 162, high-resolution parametric signal restorers 182 and an A/D conversion module 184.

Amplifiers 162 amplify the analog signals received from measurement system 170 and provide the amplified signals to high-resolution parametric signal restorers 182. As described in more detail below, each high-resolution parametric signal restorer 182 is configured to generate two or more output representations of the amplified signals received from amplifier 162. A/D conversion module 184 receives the two or more output representations from each high-resolution parametric signal restorer 182 and generates a digital signal that is passed to analysis module 190.

D. Analysis Module 190

Analysis module 190 is configured to perform various types of counting and/or analysis on the digital format data. For example, analysis module 190 can be configured to sort the particle counts into different "bins" based on relative fluorescence intensity. A bin corresponds to a range of relative fluorescence intensity. In addition, analysis module 190 may be configured to generate a histogram 194. Analysis module 190 may also perform other types of particle counting and analysis as would be apparent to a person skilled in the relevant art(s).

Analysis module 190 may be implemented in hardware, software, firmware, or a combination thereof. For example, analysis module 190 may include a processor (MCU, DSP, CPU, custom design), a field programmable gate array (FPGA), programmable logic device (PLD), discrete logic or an application specific integrated circuit ("ASIC"). Analysis module 190 may also include memory—such as read-only memory (ROM), programmable ROM (PROM), random-access memory (RAM), non-violatile RAM (NVRAM), or flash memory. The memory may hold instructions and/or data or configuration parameters for a processor, FPGA, PLD, discrete logic or ASIC to execute portions of an algorithm for measuring and analyzing particle suspended in sample 102.

II. High-Resolution Parametric Signal Restorer

High-resolution parametric signal restorer 182 is configured to generate two or more output representations of an input analog signal (such as a single input analog signal from one of PMTs 116 of FIG. 1). The two or more output representations may be used in an extended-resolution high-bandwidth digital-sampling data-acquisition system for cytometry instrumentation (such as high-resolution acquisition system 180).

In embodiments, high-resolution parametric signal restorer 182 includes (i) an input modification module that modifies an input analog signal, (ii) a multiple-gain module that provides two or more output representations of the input analog signal, wherein the two or more output representations may have different amplitudes, and (iii) a parametric compensator that derives a compensation signal from one or more of the output representations. The input modification module, the multiple-gain module and the parametric compensator may be implemented in a series embodiment or a shunt embodiment.

A. Series Embodiment

Figure 2:
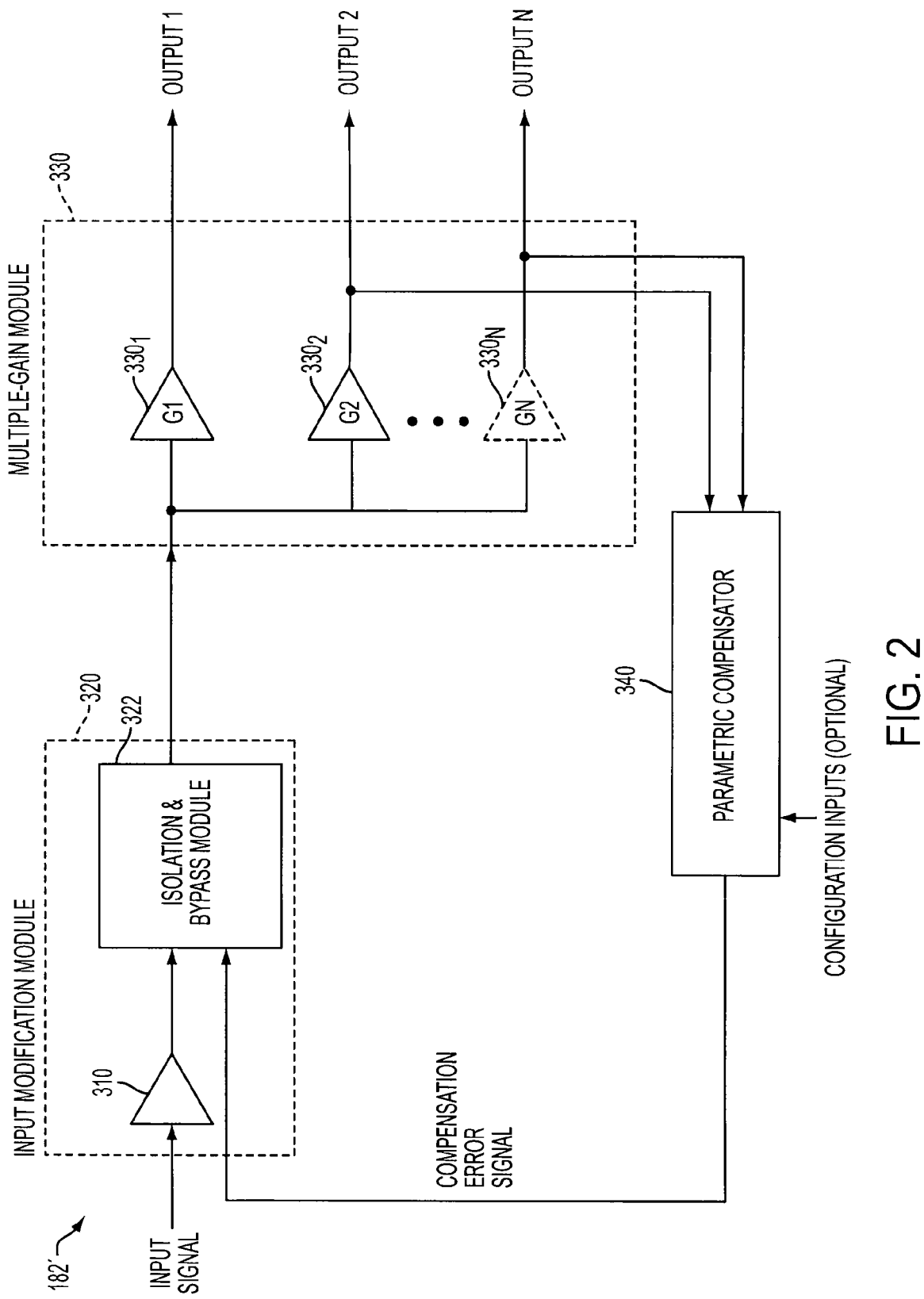
FIG. 2 illustrates a series embodiment of the high-resolution parametric signal restorer of FIG. 1.

FIG. 2 illustrates a series embodiment of high-resolution parametric signal restorer 182'. Referring to FIG. 2, high-resolution parametric signal restorer 182' includes an input modification module 320, a multiple-gain module 330, and a parametric compensator 340.

Input modification module 320 receives the input analog signal from, for example, measurement system 170 of FIG. 1. Input modification module 320 includes an input amplifier 310 and an isolation and bypass module 322. Input amplifier 310 may comprise, for example, a Bessel filter or some other type of input filter as would be apparent to a person skilled in the relevant art(s). Isolation and bypass module 322 receives two signals—the filtered input signal from input amplifier 310 and a compensation signal from parametric compensator 340. To reduce input signal perturbations (such as DC offsets, noise, temperature drifts, etc.), isolation and bypass module 322 is configured to add the compensation error signal to the filtered input signal. During calibration and/or set-up, isolation and bypass module 322 prevents the compensation error signal from being added to the filtered input signal. A control signal (not shown) may be applied to isolation and bypass module 322 to control whether the compensation error signal is added to the filtered input signal or not. In either event, the signal from isolation and bypass module 322 is passed to multiple-gain module 330.

Multiple-gain module 330 includes a plurality of output amplifiers $330_1, 330_2, \ldots, 330_N$. Each output amplifier amplifies the signal from isolation and bypass module 322 to produce an output signal, wherein the amplitudes of the respective output signals are determined by the respective gains of the output amplifiers. In this way, multiple-gain module 330 can provide a low-gain and one or more high-gain representations of the input signal, thereby extending the resolution and dynamic range of the system. The output signals are then presented to an A/D conversion module (such as A/D conversion module 184 of FIG. 1). In addition, the one or more output signals from output amplifiers $330_2, \ldots, 330_N$ are also presented to parametric compensator 340.

Parametric compensator 340 derives the compensation error signal based on the one or more output signals from output amplifiers $330_2, \ldots, 330_N$. Parametric compensator 340 includes a plurality of functional elements that independently respond to different functional parameters—such as, for example, a DC component, a time-varying component, noise, etc.—of the one or more output signals to provide the compensation error signal. For example, a first functional element may process and reduce a DC component of the one or more output signals; a second functional element may process the pulse or time-varying component of the one or more output signals; a third functional element may control the noise response; and a fourth functional element may control the pulse amplitude linearity response.

Figure 3:
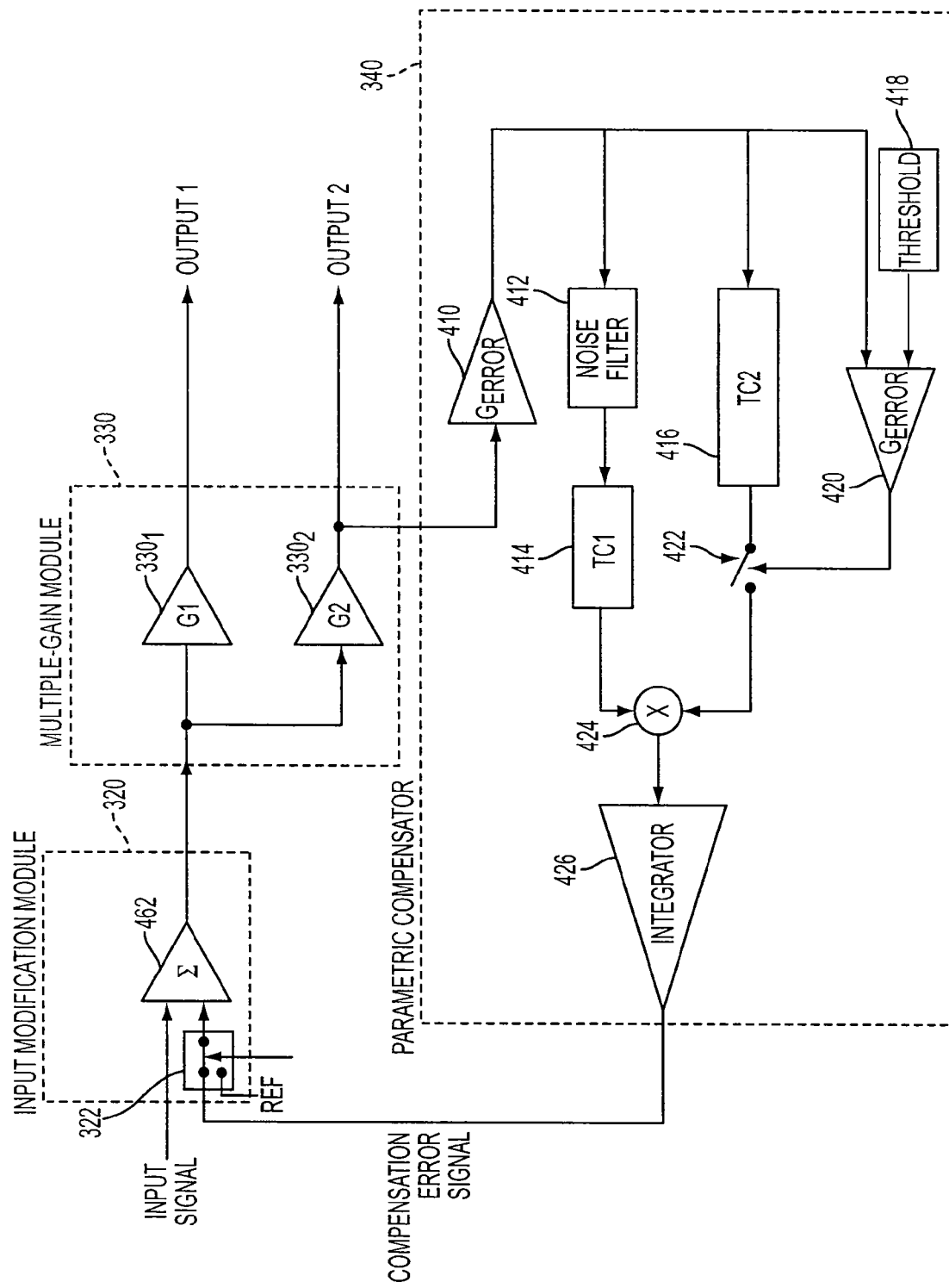
FIG. 3 illustrates a more detailed example of the high-resolution parametric signal restorer of FIG. 2.

FIG. 3 illustrates an example embodiment of input modification module 320, multiple-gain module 330, and parametric compensator 340 of high-resolution parametric signal restorer 182'. In this embodiment, parametric compensator 340 uses a dual mode restoration method for providing the compensation error signal in which a DC threshold voltage defines a low range and a high range region. The low range region typically covers the first decade of a log histogram and uses a centering restoration technique. The high range region typically covers the second through the fourth decades of a log histogram and uses a rectification technique. The DC voltage can be adjusted to change the transition point of the regions.

Figure 4B:
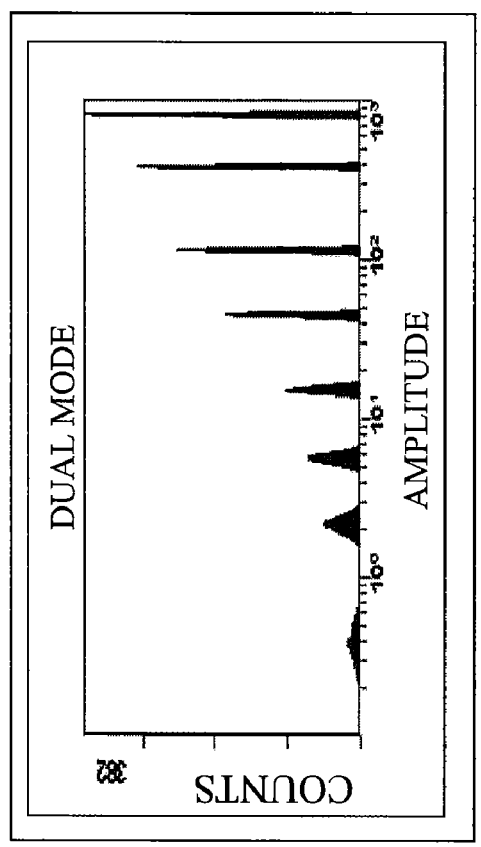
FIG. 4B illustrates a log-histogram plot of the output from a high-resolution (dual mode) baseline restorer in accordance with an embodiment of the present invention.
Figure 4A:
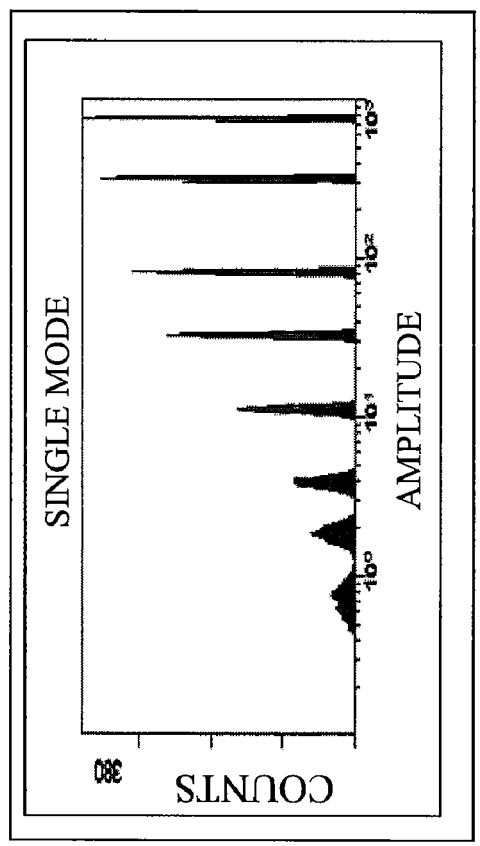
FIG. 4A illustrates a log-histogram plot of the output from a single mode baseline restorer.

An example advantage of using a dual-mode restoration method is explained with reference to the log-histogram plots of FIGS. 4A and 4B. As illustrated in FIG. 4A, a single-mode baseline restorer that uses only a rectification method causes the first population of a log histogram display to be placed further to the right than expected. This occurs because the high gain output amplifiers of multiple-gain module 330 (such as high gain amplifier $330_2$) amplify the desired signal as well as the undesired noise. The rectification method does not discriminate between the signal and the noise, and therefore rectifies the noise causing the shift in the first population of the log histogram illustrated in FIG. 4A. The dual mode restorer addresses this issue by providing a centering restoration technique for the low range region and a rectification technique for the high range region, thereby adjusting the circuit's response to the amplified noise. As a result, the display behavior of the first decade of the log histogram is also adjusted as illustrated in FIG. 4B.

Referring to FIG. 3, input modification module 320 includes a bypass module 322 and a summation module 462. Unlike the example of FIG. 2, in the example of FIG. 3 bypass module 322 is positioned before summation module 462. Bypass module 322 receives a compensation error signal from parametric compensator 340 and a reference signal.

Summation module 462 sums the compensation error signal to the input signal. The output of input modification module 320 is provided to multiple-gain module 330, which includes a low-gain amplifier $330_1$ and a high-gain amplifier $330_2$. In an embodiment, low-gain amplifier $330_1$ has a gain factor of approximately 1× and high-gain amplifier $330_2$ has a gain factor of approximately 16×. The output from high-gain amplifier $330_2$ is provided to parametric compensator 340.

As illustrated in FIG. 3, parametric compensator 340 includes an error amplifier 410, an integrator 426, and two paths that connect error amplifier 410 to integrator 426 through summation module 424. The first path is through noise filter 412 and a first component (TC1) 414 having a first time constant. The first path provides for a bipolar DC restoration function with a slow response rate, and therefore primarily reduces the DC component of the input signal. The second path is through a second component (TC2) 416 having a second time constant. The second path processes the desired signal and the undesired noise in different manners.

For the desired signal, the second path provides a unipolar response to the portion of the signal that exists in an explicit lower excursion limit domain (negative amplitude levels only) and has a time constant that is approximately forty times faster than the first path (TC1). The second path (TC2) is active only when the threshold level of threshold 418 is exceeded. The threshold 418 is set to a level substantially equal to the amplitude that represents the top of the first decade on the log display histogram. When the second path (TC2) turns off, its driving function is also turned off and the pulse peak amplitudes are not reduced. This technique enables signal fidelity and linearity for low amplitude signals.

TC2 is a fast time constant that is gated on and off by amplifier 420. The amplitude point at which amplifier 420 gates (enables) TC2 is controlled by threshold 418. The source applied to the input of TC2 and to amplifier 420 is a blend of signal and noise. TC2 is connected to summing junction 424 by switch 422 when this blend exceeds threshold 418 and has the effect of shifting the baseline reference (amplitude) of output 1 and output 2 of high resolution parametric signal restorer 182.

The unipolar shift is near the value of threshold 418 and the noise is also rectified by amplifier 420 so that the blend is presented as a unipolar quantity. This unipolar quantity may be measured by a unipolar responding acquisition system (such as sampling and A/D conversion logic 184).

TC2 is disconnected from summing junction 424 by switch 422 when the blend is less than threshold 418. The circuit then enters a mode that operates to block the DC component of the blend only. This reduces the amplitude variances of the blend and allows the noise component to locate a baseline near the system ground reference point. This mode also centers the noise component of the blend so that a unipolar responding acquisition system (such as sampling and A/D conversion logic 184) sees a portion of the noise and nearly the entire signal component. Parametric compensator 340 functions to provide the high-resolution signal component. High-resolution parametric signal restorer 182 uses the parametric compensator 340 to operate on sources that have a range of at least four decades of signal blend amplitudes.

High-resolution parametric signal restorer 182 of FIGS. 2 and 3 is effective in performing over a wide dynamic range because it is able to segment and parameterize the dynamic factors that effect the noise baseline restorer function, the DC-component nulling function, and a signal undershoot mitigator function. It performs these functions substantially simultaneously in order to provide a real-time perturbation compensation of the input signal.

In an embodiment, a second ideal diode can be connected to the input of integrator 426 to provide a more robust clamping of the positive restoration levels. Such positive levels tend to drive the displayed histogram to the left, as illustrated in FIG. 4B. This circuit can also be used to set the restoration baseline by providing a DC reference threshold. The DC reference threshold can be derived from a circuit that computes the average, maximum or minimum system noise.

In an embodiment, high-gain output amplifier $330_2$ and/or error amplifier 410 comprise Texas Instruments OPA657 operational amplifiers, which are provided by Texas Instruments Inc. of Dallas, Tex. This embodiment takes advantage of the overdrive saturation characteristics of the Texas Instruments OPA657 operational amplifier to reduce response delay and to improve the undershoot mitigation performance of parametric compensator 340. This is not intended to limit the invention, however, as other types of amplifiers may be used.

B. Shunt Embodiment

Figure 5:
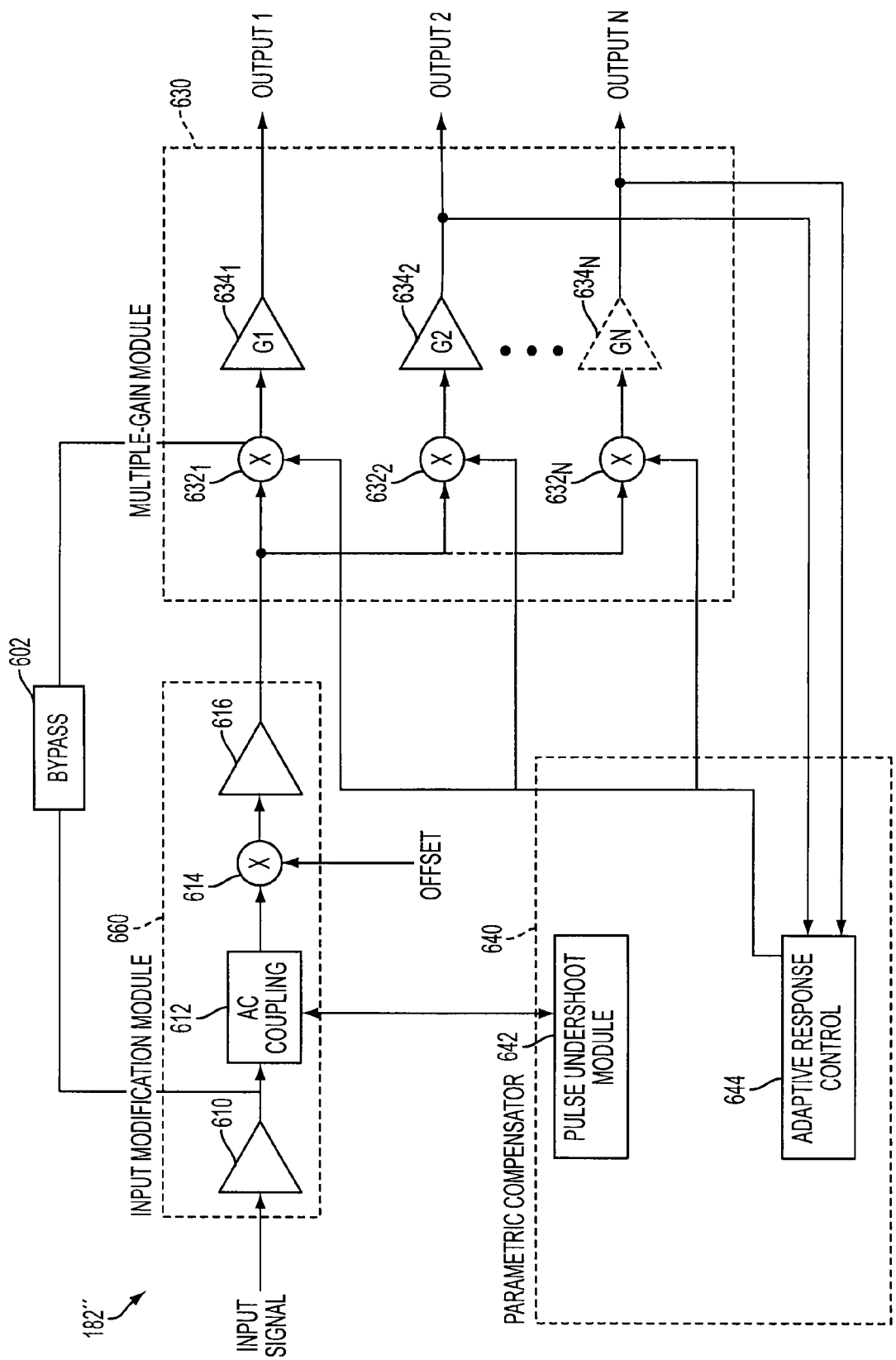
FIG. 5 illustrates a shunt embodiment of the high-resolution parametric signal restorer of FIG. 1.

FIG. 5 illustrates a shunt embodiment of high-resolution parametric signal restorer 182". The shunt embodiment includes an input modification module 660, a multiple-gain module 630, and a parametric compensator 640. Input modification module 660 receives an input signal. Multiple-gain module 630 includes (i) a low gain output amplifier $634_1$ that provides a low gain output derived from the input signal, and (ii) one or more high gain amplifiers $634_2, \ldots, 634_N$ that respectively provide one or more high gain output signals derived from the input signal. Parametric compensator 640 provides compensation, such as pulse undershoot recovery and adaptive response control for temperature variations and noise. First, a pulse undershoot recovery signal is derived by pulse undershoot module 642 and interacts with the time-varying signal at AC coupling 612. Second, an adaptive response control 644 derives a compensation signal from the one or more high gain output signals, and applies the compensation signal to the input signal via summation modules $632_1, 632_2, \ldots, 632_N$.

A bypass circuit 602 provides a restoration bypass function. This bypass function is useful when determining channel and sensor offsets during initialization and system calibration.

Referring to FIG. 5, input modification module 660 includes an input filtering amplifier 610, an AC coupling 612, a summation module 614, and an output filtering amplifier 616. Input amplifier 610 may comprise, for example, a Bessel filter or some other type of input filter as would be apparent to a person skilled in the relevant art(s). AC coupling circuit 612 receives the filtered input signal from input amplifier 610, and couples the filtered input signal to multi-gain module 630 via summation module 614 and amplifier 616. In an embodiment, amplifier 616 comprises a non-inverting amplifier.

Multiple-gain module 630 includes (i) a plurality of summation modules $632_1, 632_2, \ldots, 632_N$, (ii) a low gain output amplifier $634_1$, and (iii) one or more higher gain output amplifiers $634_2$ through $634_N$. In an embodiment, multiple-gain module 630 includes two output amplifiers: low output amplifier $634_1$, having a gain of approximately 1×; and high output amplifier $634_2$, having a gain of approximately 16×. The output of the one or more higher gain amplifiers $634_2, \ldots, 634_N$ is (are) coupled to parametric compensator 640.

Parametric compensator 640 includes a pulse undershoot module 642 and an adaptive response control 644. As mentioned above and described in more detail below, pulse undershoot module 642 provides pulse undershoot recovery and adaptive response control 644 corrects for input noise components and thermal drift associated with low gain amplifiers 616 and 634, and the one or more high gain amplifiers $634_2, \ldots, 634_N$.

i. Pulse Undershoot Module 642

FIG. 6 illustrates example components of pulse undershoot module 642, including pulse undershoot recovery circuit 784 and pulse undershoot recovery regulator 782. Pulse undershoot recovery circuit 784 provides pulse undershoot recovery. Pulse undershoot recovery regulator 782 reduces errors arising from inherent offsets produced by one or more amplifiers of pulse undershoot recovery circuit 784.

Pulse undershoot arises due to AC coupling 612. A time-varying signal coming into high-resolution parametric signal restorer 182" is AC coupled to the outputs via AC coupling 612. As a result, voltage may build up across AC coupling 612. This voltage appears as an undershoot tail at amplifiers 634 when the time-varying signal is removed. The tail slowly diminishes with the time constant of AC coupling 612. This is undesirable since a second pulse may follow the first pulse with a small time delay. The baseline distortion caused by the undershoot tail will compromise the amplitude accuracy of the second pulse. Pulse undershoot recovery circuit 784 and pulse undershoot recovery regulator 782 function to reduce the pulse undershoot recovery time. Any DC voltage preceding AC coupling 612 is blocked.

For example, FIG. 8 graphically illustrates how pulse undershoot recovery circuit 784 and pulse undershoot recovery regulator 782 function to reduce pulse undershoot. FIG. 8 includes two traces representing two separate channels—namely, a first trace 902 and a second trace 904. The first trace 902 illustrates the response at high gain output $634_2$ when pulse undershoot recovery circuit 784 and pulse undershoot recovery regulator 782 are disconnected. The second trace 904 illustrates the response at high gain output $634_2$ when pulse undershoot recovery circuit 784 and pulse undershoot recovery regulator 782 are connected. In each trace, a large pulse 910 is followed by a small pulse 920. The amplitude ratio of the large pulse 910 to small pulse 920 is approximately 280:1.

The recovery tail is apparent in the first trace 902. This recovery tail causes the small pulse 920 to improperly register a slightly lower amplitude. As a result, the small pulse 920 may be treated as simply noise, when it in fact represents a desired event.

In contrast, the second trace 904 illustrates that pulse undershoot recovery circuit 784 and pulse undershoot recovery regulator 782 function to quickly restore the baseline reference level after the large pulse. In this way, the amplitude of the small pulse is properly measured, thereby enabling the detection and analysis of the small pulse. Accordingly, the shunt embodiment of high-resolution parametric signal restorer 182" advantageously presents all information about an event pulse to signal capture circuits (such as analysis module 190). In harmony with AC coupling 612, pulse undershoot recovery circuit 784 acts as a signal rectifier and provides rapid baseline recovery. This can be a distinct advantage over baseline centering restoration circuits. Since all the signal information above the recovery reference is restored, pulse undershoot recovery circuit 784 and pulse undershoot recovery regulator 782 enable accurate signal linearity measurements—as illustrated, for example, in FIG. 10.

Pulse undershoot recovery regulator 782 may be implemented in any of the following example embodiments:
1. A microprocessor controlled offset adjust using system feedback and analysis to control the level of any offset adjust.
2. A hardware-based feedback offset element that monitors the $V_{in}$ offset of pulse undershoot recovery circuit 784 and introduces an opposite voltage to substantially null this error source. This also provides temperature compensation for this loop.

3. A manual adjust circuit that introduces offsets as the pulse recovery is monitored.
4. A fixed value of introduced offset to remove bulk offsets due to one or more amplifiers of pulse undershoot recovery circuit 784 and bias it to operate with appropriate response.
5. Any combination of the above 1-4 implementations that provide appropriate performance of pulse undershoot recovery circuit 784.

These examples are presented for illustrative purposes only, and not limitation.

FIG. 9A illustrates an example implementation of pulse undershoot recovery circuit 784. Pulse undershoot recovery circuit 784 includes operational amplifier 1002. The negative input of operational amplifier 1002 is coupled to AC coupling 612 through resistor R112, and the positive input of operation amplifier 1002 is coupled to ground through resistor R122. The positive input also receives a small hysterisis signal through resistor R110.

After a negative pulse is received by AC coupling 612, operational amplifier 1002 conducts through diode D110. Accordingly, current flows through resistor R112. This allows charge to build up on AC coupling 612. When the input pulse is removed, the stored charge in AC coupling 612 appears positive relative to R112 but current cannot flow into D110 and amplifier 1002 is forced to conduct through D112. This action rapidly discharges AC coupling 612 due to the small diode on resistance of D112, thereby quickly reducing the undershoot recovery tail as illustrated in FIG. 8. The undershoot tail illustrated in FIG. 8 is the inverted response of that which occurs at AC coupling 612. Although embodiment of pulse undershoot recovery circuit 784 of FIG. 9A processes negative pulses with positive overshoot, it is the inverted output signal presented to sampling A/D conversion logic 184 that defines the polarity of signal traces as shown in FIG. 8. Changing the polarity of diodes D110 and D112 would permit the opposite effect at AC coupling 612.

Unfortunately, operational amplifier 1002 may not be ideal. For example, the negative input may have a small offset (such as, for example, 0.8 mV) due to an input offset voltage of amplifier 1002. As a result, the negative input of operational amplifier 1002 may not reference to zero volts even though the positive input is approximately at ground after a pulse (e.g., the positive input may be at approximately ground plus a small hysteresis below 100 micro-volts). Consequently, the discharge of AC coupling 612 may stop premature of its steady state level or overshoot its steady state level, depending on the polarity of the amplifier offset. This will cause a small recovery tail that discharges with the time constants of the AC coupling components. The steady state level is the voltage at the output of AC coupling 612 when only DC voltage is present at input amplifier 610, neglecting any noise present.

FIG. 9B illustrates an embodiment of pulse undershoot recovery circuit 784 and pulse undershoot recovery regulator 782. Resistor R120 of pulse undershoot recovery regulator 782 and resistor R122 form a resistor divider and are connected to a negative supply (such as −6V). This divider functions to reduce offsets caused by the non-ideal nature of operational amplifier 1002 and forces the offset at the negative input of operational amplifier 1002 to be near zero reference or slightly negative. This will serve to have AC coupling 612 discharge closer to steady state.

FIG. 9C illustrates another embodiment of pulse undershoot recovery circuit 784 and pulse undershoot recovery regulator 782. Amplifier U1004 is coupled to pulse undershoot recovery circuit 784 through resistor R126 to monitor the negative input terminal of amplifier U1002. Amplifier U1004 is selected to have an input offset voltage lower than that of amplifier U1002 and to have a low input bias current. In an embodiment, amplifier U1004 comprises an AD8610BRZ operational amplifier offered by Analog Devices, Inc. of Norwood, Mass. The embodiment of pulse undershoot recovery regulator 782 illustrated in FIG. 9C permits the negative terminal of amplifier U1002 to be controlled by the offset of amplifier U1004 plus the small offset at the positive terminal of amplifier U1004. This is accomplished by the negative feedback loop that pulse undershoot regulator 782 creates. Based on the offset of amplifier U1004, AC coupling 612 can reach steady state more predictably, keeping overshoot and undershoot errors very small. Pulse undershoot recovery regulator 782 also tracks temperature variations that occur with the input offset voltage of amplifier U1002.

Figure 11A:
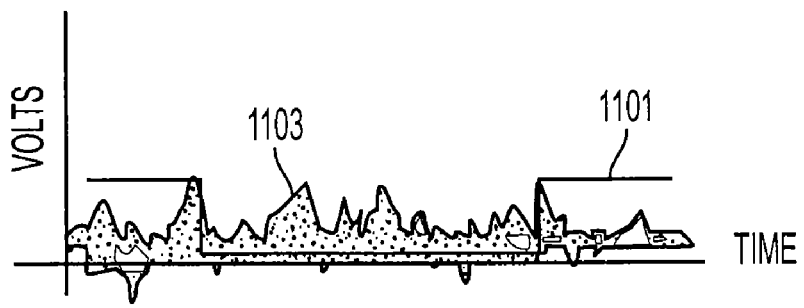

Although pulse undershoot module can reduce pulse undershoot, at least two issues still remain. First, temperature variations in output amplifiers 634 of multiple-gain module 630 and amplifier 616 of input modification module 660 may not be compensated for during an instrument run cycle. Prior to run, offsets can be calibrated out by firmware but during a run cycle drifts may occur. A second issue arises when parameter baseline noise levels increase. Because the shunt baseline restorer illustrated in FIG. 5 is a rectifying circuit, it rectifies the desired signal and the undesired noise. Since the noise is rectified and not centered at ground, integration of this noise signal will yield a larger net positive value over a complete capture window than otherwise. An example capture window 1101 is illustrated in FIG. 11A. The effect of rectified noise is illustrated in FIG. 4A, wherein the system background noise is the lowest population and both the acquired noise and signal populations are moved to the right in the first decade of a four decade log acquisition histogram. The most observable effect will be to narrow the distance between the first- and second-lowest populations. Adaptive response control 644 functions to address both of these issues.

ii. Adaptive Response Control 644

Adaptive response control 644 dynamically operates in different modes to address DC offsets, thermal drift, and signal noise. As illustrated in FIG. 5, adaptive response control 644 receives input from the one or more high gain output amplifiers $634_2, \ldots, 634_N$. In this way, adaptive response control 644 provides high gain closed loop DC offset correction that is proportional to the one or more high gain output amplifiers $634_2, \ldots, 634_N$.

Adaptive response control 644 does not respond to pulse signals. Typical closed loop response mechanisms respond to pulse signals when correcting for DC errors, thereby generating pulse response recovery errors. Such pulse response errors can be additive with repetition rate introducing secondary output offset errors. Importantly, adaptive response control 644 responds to noise levels—not pulse signals—and shifts output baseline to reduce noise above ground. Additionally, adaptive response control 644 does not add unnecessary bias under low noise conditions. In an embodiment, adaptive response control 644 includes a programmable offset control 760 (see FIG. 6), allowing software or other programmable logic to change the net offsets of output amplifiers 634, if necessary.

FIG. 6 illustrates example components of adaptive response control 644—including an adaptive response filter 762, a bias operating point module 764, a first proportional offset 766, and a second proportional offset 768. Adaptive response control 644 may also optionally include a programmable offset control 760, which can be programmed from a system interface 780. Adaptive response control 644 adjusts the DC output based on the input it receives from the one or more higher gain amplifiers $634_2$ through $634_N$ and the input it receives from programmable offset control 760. If the programmed offset is zero, the output offsets are controlled by the high gain amplifiers used in a feedback loop with adaptive control 644.

Figure 7:
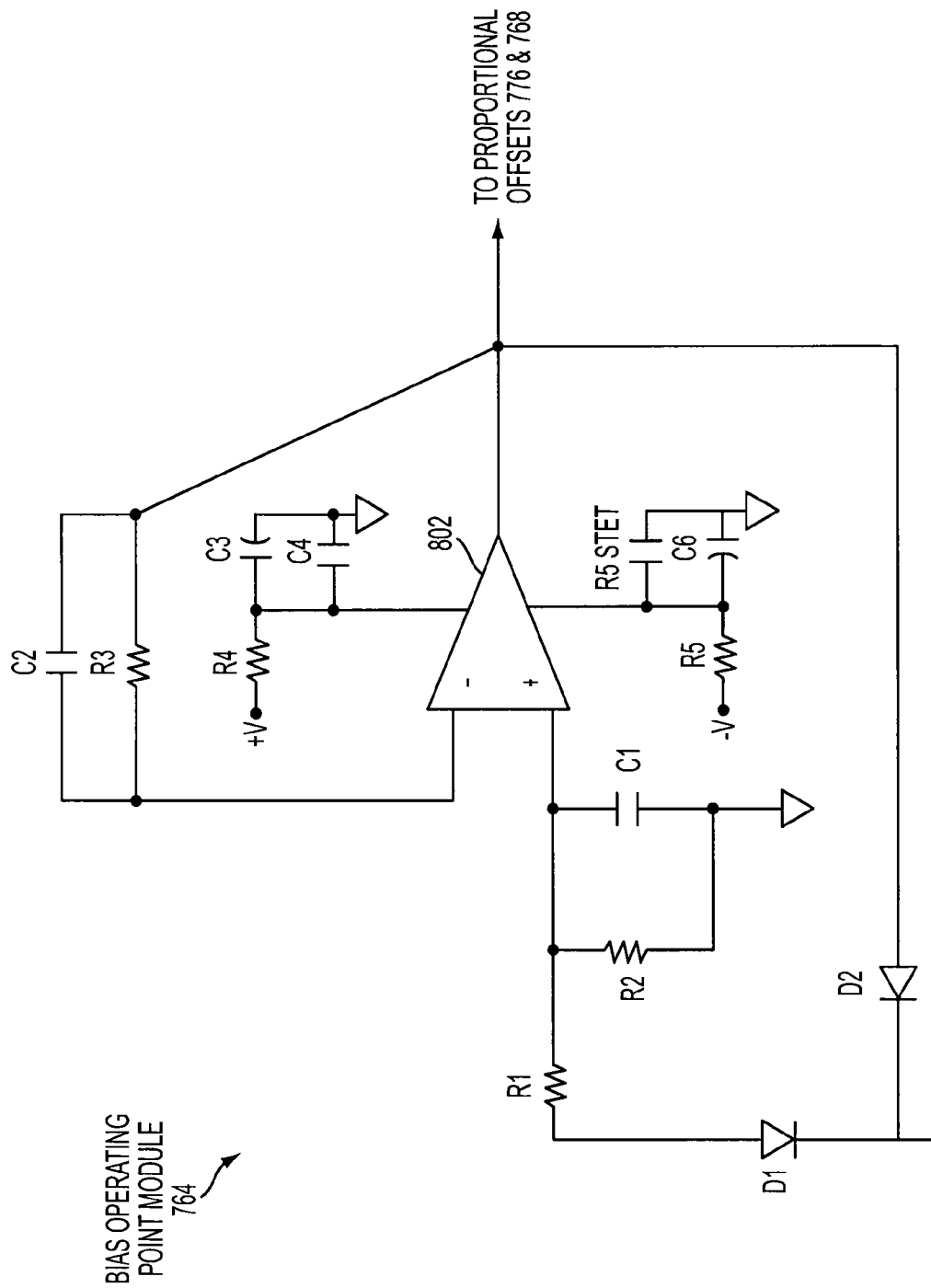
FIG. 7 illustrates an embodiment of a bias operating point module depicted in the high-resolution parametric signal restorer of FIG. 6.

FIG. 7 illustrates an example bias operating point module 764. As illustrated in FIG. 7, bias operating point module 764 includes an operational amplifier 802. The negative input of operational amplifier 802 is coupled to the output through capacitor C2 and resistor R3. The positive input of operational amplifier 802 is coupled to a hold capacitor C1, a discharge resistor R2, and a charge resistor R1. Adaptive response filter 762 is coupled in series to the positive input of operational amplifier 802 through a diode D1 and charge resistor R1, and is coupled to the output of operational amplifier 802 through diode D2.

The operation of bias operating point module 764 is now described with reference to FIGS. 6 and 7. Bias operating point module 764 charges to a predetermined voltage (for example, approximately −1.2V) as set by the offset summed into amplifier 616 by summation module 614. The offset introduced into amplifier 616 is low, but is amplified by high gain output amplifier $634_2$. The amplified signal is presented to adaptive response filter 762, which amplifies DC with high gain. The polarity of the offset introduced at amplifier 616 is such that adaptive response filter 762 forward biases diode D1 and hold capacitor C1, permitting hold capacitor C1 to charge with a fast time constant through resistor R1.

When bias operating point module 764 reaches full charge, diode D1 becomes reverse biased and turns off. By this time, the offset introduced into amplifier 616 is removed from all output amplifiers 634 and high gain output amplifier $634_2$ is set at a reference point. The polarity of diode D1 is determined such that when a pulse is introduced to the input of adaptive response control 644, adaptive response filter 762 outputs a signal that reverse biases diode D1 preventing hold capacitor C1 from being charged by the pulse. The voltage decay of hold capacitor C1 is set using a large time constant (determined by the value of resistor R2) compared to the charge time constant (determined by the value of resistor R1). This allows a little, but controllable, droop that is determined from diode leakage, amplifier 802 bias current requirements, and/or the time-constant discharge of resistor R2 and capacitor C1. The recovery from this small droop is proportionally rapid and based on the time constant set by resistor R1 and capacitor C1. Importantly, the polarity of the pulse undershoot initiated by pulse undershoot recovery circuit 784 is such that it helps bias operating point module 764 maintain stability. Being closed loop, adaptive response control 644 and high gain output amplifier $634_2$ seek to maintain DC stability.

The proportional offsets 766 and 768 are set large to allow the voltage from bias operating point module 764 to become large. With large proportional offsets 766 and 768, the large voltage developed by bias operating module 764 displaces the relatively small offset introduced at amplifier 616. This technique reduces errors introduced by the amplifiers included in adaptive response control 644 and any droop associated with the elements of bias operating point module 764 under dynamic operating conditions. These errors are effectively reduced by the large resistive elements of proportional offsets 766 and 768 inputs which divide down the signals presented to output amplifiers $634_1$ and $634_2$, respectively.

In summary, adaptive response filter 762 and bias operating point module 764 are designed such that if noise is detected, bias operating point module 764 discharges hold capacitor C1 (FIG. 7) relative to the circuit time constants, noise levels, and the clip and clamp levels of adaptive response filter 762. This shifts the DC operating level of output amplifiers 634 a small amount and reduces the average noise above ground measured by the remainder of the data acquisition system (e.g., high-resolution acquisition system 180).

Figure 11B:
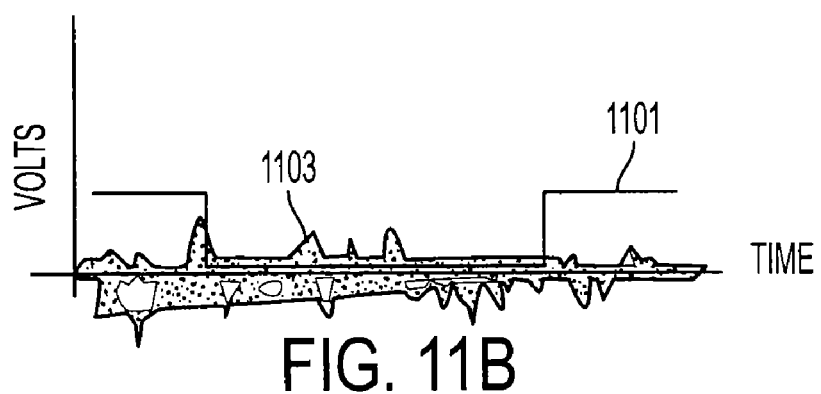
Figure 11C:
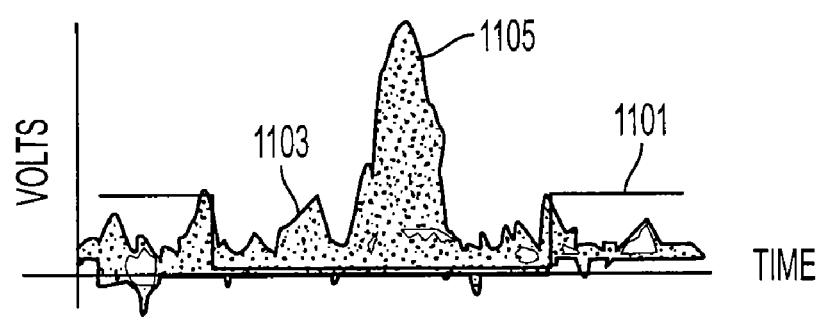
Figure 11D:
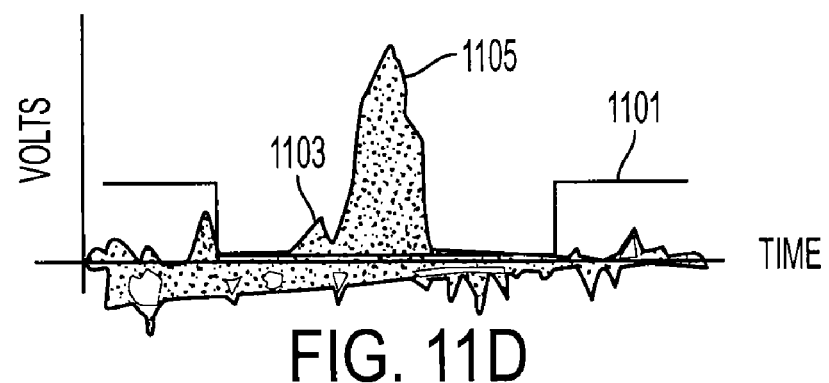

For example, FIGS. 11A-D illustrate how adaptive response filter 762 and bias operating point module 764 operate to shift the DC operating level of output amplifiers 634 a small amount and reduce the average noise above ground as measured by the remainder of the data acquisition system (e.g., high-resolution acquisition system 180). FIG. 11A depicts a noise level 1103 with respect to an event capture window 1101, when adaptive response filter 762 and bias operating point module 764 are not used. FIG. 11B depicts noise level 1103 with respect to event capture window 1101, when—in contrast to the situation depicted in FIG. 11A—adaptive response filter 762 and bias operating point module 764 function to reduce the average noise level of noise level 1103. Similar to FIG. 11A, FIG. 11C depicts noise level 1103 and a pulse 1105 with respect to event capture window 1101, when adaptive response filter 762 and bias operating module 764 are not used. Similar to FIG. 11B, FIG. 11D depicts noise level 1103 and pulse 1105 with respect to event capture window 1101, when adaptive response filter 762 and bias operating point module 764 function to reduce the average noise level of noise level 1103. In doing so, the net integrated noise signal is less and the displayed histogram populations will appear as in FIG. 4B. With less noise integrated above ground, the lowest population of FIG. 4B will move proportionally more to the left relative to the movement of the other populations.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A system for processing electronic signals, comprising:
a multi-output module configured to simultaneously provide a reference gain output signal to a restored signal receiving module and one or more higher gain output signals to a parametric compensator, wherein the multi-output module includes a first amplifier configured to receive an input signal, wherein the multi-output module includes one or more higher gain amplifiers respectively configured to receive the input signal, wherein the first amplifier is configured to provide a reference gain output signal responsive to the input signal, and wherein the one or more higher gain amplifiers are respectively configured to provide one or more higher gain output signals responsive to the input signal and having a larger gain than the reference gain output signal; and the parametric compensator configured to receive the one or more higher gain output signals and to provide a compensation error signal responsive to functional parameters of the one or more higher gain output signals, wherein the input signal is modified based on the compensation error signal.

2. The system of claim 1, wherein the one or more higher gain output signals have a direct current (DC) component, and wherein the parametric compensator comprises a first modifier configured to reduce the DC component of the one or more higher gain output signals.

3. The system of claim 2, wherein the first modifier comprises a noise filter and a time constant module configured to reduce the DC component of the one or more higher gain output signals.

4. The system of claim 1, wherein the one or more higher gain output signals include a pulse undershoot amplitude, and wherein the parametric compensator comprises a first modifier configured to reduce the pulse undershoot amplitude included in the one or more higher gain output signals.

5. The system of claim 4, wherein the one or more higher gain output signals include an amplitude, and wherein the first modifier comprises a time constant module that reduces the pulse undershoot amplitude when the amplitude of the one or more higher gain output signals exceeds a threshold.

6. The system of claim 1, further comprising:
an input signal modification module that modifies the input signal based on the compensation error signal to reduce perturbations included in the input signal.

7. The system of claim 6, wherein the input signal modification module comprises:
a passive isolation element configured to couple the input signal to an input of the multi-output module thereby forming a compliant point of the system;
wherein the compensation error signal is forced to appear at the compliant point to reduce the perturbations included in the input signal.

8. A system for processing electronic signals, comprising:
a multi-output module that provides a reference gain output signal and one or more higher gain output signals based on an input signal; and
a parametric compensator that responds to functional parameters of the one or more higher gain output signals to provide a compensation error signal,
wherein the input signal is modified based on the compensation error signal, and
wherein the functional parameters of the one or more higher gain output signals include an optical noise component, and wherein the parametric compensator includes a first modifier configured to shift a reference position of the optical noise component included in the one or more higher gain output signals.

9. A system for processing electronic signals, comprising:
a multi-output module that provides a reference gain output signal and one or more higher gain output signals based on an input signal;
a parametric compensator that responds to functional parameters of the one or more higher gain output signals to provide a compensation error signal,
an input signal modification module that modifies the input signal based on the compensation error signal to reduce perturbations included in the input signal, and
wherein the input signal modification module comprises:
a summation and isolation module configured to (1) add the compensation error signal to the input signal when a calibration signal is not present and (2) prevent the compensation error signal from being added to the input signal when the calibration signal is present.

10. A method for processing electronic signals, comprising:
(a) simultaneously providing, using respective amplifiers configured to receive an input signal, a reference gain output signal to a restored signal receiving module, and one or more higher gain output signals to a parametric compensator, wherein the higher gain output signals have larger respective gains than the reference gain output signal;
(b) providing a compensation error signal responsive to functional parameters of the one or more higher gain output signals; and
(c) modifying the input signal based on the compensation error signal.

11. The method of claim 10, wherein (b) comprises reducing a direct current (DC) component of the one or more higher gain output signals to provide the compensation error signal.

12. The method of claim 11, wherein the reducing the DC component of the one or more higher gain output signals comprises filtering the one or more higher gain output signals through a noise filter and a time constant module to reduce the DC component of the one or more higher gain output signals.

13. The method of claim 10, wherein (b) comprises reducing a pulse undershoot amplitude included in the one or more higher gain output signals to provide the compensation error signal.

14. The method of claim 13, wherein the reducing the pulse undershoot amplitude comprises filtering the one or more higher gain signals through a time constant module when the amplitude of the one or more higher gain output signals exceeds a threshold.

15. The method of claim 10, wherein step (c) comprises:
(c1) forming a compliant point in a circuit; and
(c2) forcing the compensation error signal to appear at the compliant point to reduce the perturbations included in the input signal.

16. A method for processing electronic signals, comprising:
(a) forming a reference gain output signal and one or more higher gain output signals based on an input signal;
(b) responding to functional parameters of the one or more higher gain output signals to provide a compensation error signal, wherein (b) comprises shifting a relative position of an optical noise component included in the one or more higher gain output signals when displayed on a log-histogram plot; and
(c) modifying the input signal based on the compensation error signal.

17. A method for processing electronic signals, comprising:
(a) farming a reference gain output signal and one or more higher gain output signals based on an input signal;
(b) responding to functional parameters of the one or more higher gain output signals to provide a compensation error signal; and
(c) modifying the input signal based on the compensation error signal, wherein (c) comprises:
(c1) adding the compensation error signal to the input signal when a calibration signal is not present; and
(c2) preventing the compensation error signal from being added to the input signal when the calibration signal is present.

18. A high-resolution signal restoration system for processing signals from a measurement instrument, comprising:

a first combining module that combines an input signal and a compensation error signal to provide a combined signal;

a first amplifier, having a first gain that provides a first amplified signal based on the combined signal;

a second amplifier, having a second gain that is different from the first gain, that provides a second amplified signal based on the combined signal; and a feedback that generates the compensation error signal based on the second amplified signal, the feedback including a first direct current (DC) restoration module having a first time constant and configured to reduce a DC component of the second amplified signal to provide a first processed signal, a second DC restoration module having a second time constant that is different from the first time constant and configured to reduce the DC component of the second amplified signal to provide a second processed signal, and a feedback output module that provides either the first processed signal or a combination of the first and second processed signals as the compensation error signal based on a threshold.

* * * * *